United States Patent [19]

Gindler

[11] 3,953,297
[45] Apr. 27, 1976

[54] DETERMINATION OF AMYLASE
[75] Inventor: E. Melvin Gindler, Rockford, Ill.
[73] Assignee: Pierce Chemical Company, Rockford, Ill.
[22] Filed: Nov. 15, 1974
[21] Appl. No.: 524,246

Related U.S. Application Data
[62] Division of Ser. No. 335,736, Feb. 26, 1973, Pat. No. 3,869,348.

[52] U.S. Cl. ................... 195/103.5 R; 195/103.5 C
[51] Int. Cl.² ........................................ G01N 31/14
[58] Field of Search ............... 195/103.5 R, 103.5 C

[56] References Cited
UNITED STATES PATENTS
3,413,198  11/1968  Deutsch ...................... 195/103.5 R
3,758,384   9/1973  Babson et al. ............... 195/103.5 R OTHER PUBLICATIONS
Searcy et al., The American Journal of Clinical Pathology, Vol. 46, No. 5, pp. 582–586 (1966).

Primary Examiner—Alvin E. Tanenholtz

[57] ABSTRACT

A method for the determination of amylase activity and a useful highly stable color reagent aqueous solution therefore are disclosed. The solution comprises, as a color reagent, an aromatic nitro containing compound such as 3,5-dinitrosalicyic acid, a color stabilizing chelating compound such as ethylenediaminetetraacetic acid, and a hydroxide base. Eliminating the necessity for centrifuging prior to the determination of amylase activity can be achieved by including potassium hydroxide for at least a part of the base in the solution.

10 Claims, No Drawings

DETERMINATION OF AMYLASE

This is a division, of application Ser. No. 335,736, filed Feb. 26, 1973, now U.S. Pat. No. 3,869,348.

The present invention relates to the determination of amylase activity. More particlarly, it relates to an improved saccharogenic procedure for the determination of amylase.

Amylase is known to catalyze the hydrolysis of starch resulting in the formation of lower glucose polymers such as maltose, trioses, etc., hereafter referred to as lower sugars. It is known that the lower sugars can, under appropriate conditions, reduce certain organic compounds. Thus, by using an organic compound which exhibits a color change on reduction by products resulting from the hydrolysis of starch, customary colorimetric technique can be used to indicate the degree to which starch hydrolysis has occurred and, in turn, the quantity of amylase orginally present. The determination of amylase is medically important since the presence of high levels of amylase in blood serum or other biologic fluids may indicate pancreatitis.

A saccharogenic procedure which follows the rate of lower sugar production after the addition of a serum sample to a starch substrate has been frequently employed in determining amylase activity. In this procedure, the color reagent (reducible by the lower sugars) is added to the starch-serum mixture after a predetermined amount of time. Addition of the color reagent terminates the enzyme catalyzed hydrolysis of starch and, thereafter, the degree of hydrolysis which has been achieved is indicated by the extent to which the added quantity of color reagent is reduced by the lower sugars produced. Amyloclastic methods, which follow the rate at which starch or turbidity of a starch-serum mixture disappears, are also used for indicating amylase activity. However, it is believed that the present invention is principally applicable to saccharogenic procedures.

The use of dinitrosalicylic acid (DNSA) for the determination of reducing sugar has been known for many years (e.g., Sumner and Graham, J. Biol. Chem. 47, 5 (1921) and Miller, Analytical Chemistry, Vol. 31, 426–428 (1959)). The use of DNSA to saccharogenically determine amylase activity is also known (e.g., Searcy et al., The American Journal of Clinical Pathology, 46, 582–586 (1966)). Generaly, amylase activity is reported in Somogyi units. By definition, a Somogyi unit of amylase activity equals 0.01 mg of reducing substance, expressed as glucose, generated by incubating 1.0 ml of serum according to the Somogyi procedure which is described in J. Biol. Chem. 125, 399 (1938).

Concerning the use of DNSA, Miller, supra, indicates that for the determination of reducing sugar, ingredients other than DNSA are necessary. These include Rochelle salt (potassium sodium tartrate) to prevent dissolution of oxygen, phenol to increase the amount of color produced and to balance the effect of phenol encountered in urine, sodium bisulfite to stabilize the color obtained in the presence of phenol, and sodium hydroxide to permit the reducing action of glucose on DNSA. The article indicates that the use of thhe Rochelle salt, while being essential to color stability, interferes with the protective action of the sulfite and that this may be resolved either by eliminating the Rochelle salt from the color reagent solution used and adding it after color is developed or by adding glucose to compensate for losses sustained in the presence of the Rochelle salt.

Searcy et al., supra, appears to describe a procedure using DNSA color reagent, sodium hydroxide and Rochelle salt without the presence of phenol and sulfite and states that the reagent iss stable for at least six months when stored in a tightly sealed amber bottle to prevent undue exposure to light and air. The absence of the bisulfite is believed to result in an inability to indicate small levels of amylase particularly with starch substrates which have been pretreated to remove reducing groups such as aldehydes.

A procedure using an essentially non-reducing starch substrate has the advantage that small errors in substrate volume produce virtually insignificant error in the final result. Also, many colorimeters are not accurate nor can be set at absorbance = 0 with reagent blanks of high absorbance and reducing starches tend to give such high absorbance. However, an initial disadvantage of using non-reducing starches is that the straight graph lines (glucose v. absorbance) do not go through the origin; a very common problem with 3,5-dinitrosalicylate. The addition of phenol and sulfite to the system causes the straight graph lines to approach more closely the origin, thereby enhancing the ability to detect low levels of reducing sugar and, in turn, low concentrations of amylase.

In its broadest aspects, it is an object of the present invention to provide an improved procedure for determining amylase activity which realizes the benefits of using reducibile color reagents such as DNSA but in which the presence of Rochelle salt with its attendant problems is not necessary in order to achieve color stability. More particularly, an object of the invention resides in providing a highly stable color reagent solution which is effective in indicating small levels of amylase concentration in biologic fluids. A more specific object resides in providing a lower sugar reducible reagent solution including sulfite ions to permit effective measurements of small concentrations of amylase and wherein the reagent solution is itself stable for extended periods of time. Yet a further object is to provide a reagent solution wherein the subsequently formed reduced solution has a color which is stable for many hours.

As indicated above, the presence of phenol is also desirable in procedures using reducible color reagents. However, phenol is unstable in the presence of air, poisonous, and exhibits an unpleasant odor. Accordingly, a further object of the present invention is to provide a color reagent solution which is sensitive in detecting amylase but wherein phenol iss not present.

Referring again to procedures using DNSA, it is generally necessary to heat the solution formed after the addition of DNSA to the hydrolyzed starch substrate in order to effect reduction. It has been noted that upon subsequent cooling when a biologic fluid such as blood serum is present, particles sometimes appear creating turbidity and necessitating centrifuging before spectrophotometric analysis. Thus, a further object of the present invention is to provide a procedure and, in turn, a improved color reagent solution, wherein particles are not formed in significant quantity and the necessity for centrifuging is obviated.

Briefly stated, all of the objects and aims of the present invention can be realized by using a reducible color reagent solution which contains, in addition to the color reagent itself, ethylenediaminetetraacetic acid (EDTA), sodium salicylate, sodium sulfite, sodium hydroxide, and potassium hydroxide. Surprisingly, the use of EDTA, instead of the Rochelle salt, has been found effective in providing a highly color stable solution both as prepared and after addition to the hydrolyzed starch substrate. There is no apparent interference with the protective action of the sulfite. In addition, EDTA is believed to effectively chelate multivaliant metal ions which may be present in the serum and thus prevent them from precipitating or otherwise interferring. The sodium salicylate appears to enhance the sensitivity of the measurement, but its use is not accompanied by those disadvantages identified above associated with the presence of phenol. Lastly, the presence of potassium hydroxide eliminates the problem of turbidity after heating and thus centrifuging is not necessary.

The following example illustrates the present invention.

PREPARATION OF STARCH SUBSTRATE

Twenty grams of soluble potato starch is dissolved in 400 ml deionized water with heat and stirring. The solution is cooled to room temperature and 0.60 grams of $KBH_4$ is added and the solution stirred for two hours at room temperature. Then 1.6 ml of acetone are added and the solution stirred for an additional twenty minutes. As described by Strumeyer, Analytical Biochemistry 19, 61– (1967), treatment with borohydride removes aldehyde groups their precursors by converting the terminal glucosyl groups in the starch to non-interferring glucitol residues.

The starch solution so prepared is then diluted with water to about 1.9 liters and the following ingredients which are a combination of peservatives, accelerators and buffers are added while the solution is stirred.

5.0 ml. 37% HCHO (Reagent)
4.0 grams Potassium Sorbate
7.50 grams $KH_2PO_4$
8.00 gm. $Na_2HPO_4$
8.0 grams NaCl
4.0 grams NaF The total volume of the resulting solution is then adjusted to 2 liters by addition of deionized water and when stored at room temperature is stable for at least about six months.

PREPARATION OF DNSA COLOR REAGENT SOLUTION

The following reagents are added to water to give 1 liter of solution with the DNSA being added first and the hydroxides added last.

1.85 gm. 3,5-Dinitrosalicylic Acid . $H_2O$
50 gm. $Na_2CO_3$*
20 gm Na Salicylate
20 gm. $Na_2SO_3$
1.5 gm. $Na_2H_2EDTA$ . $2H_2O$ (Dihydrate of disodium salt of ethylenediaminetetraacetic acid)
20 ml. 19 M NaOH
40 ml. 45% potassium hydroxide

* Add to increase ionic strength to a high level and thus prevent significant ionic strength variations.

AMYLASE DETERMINATION

Two 13 ×100 mm test tubes, one marked "T" (test) and the other "B" (blank) are employed using the following procedures. Control serum of high amylase activity (such as Warner-Chilcott "Versatol E" or Dade "Moni-trol II" or "Enza-trol") is used as the standard. Normal (isotonic) saline (e.g., the sodium chloride solution intended for injection) solution can be used to prepare dilutions of the serum, for the preparation of a colorimetric calibration graph (absorbance versus amylase activity). Saccharogenic procedure values given with the control serum are used. An alternative standard is serum previously analyzed by means of a reference procedure. A further alternative standard is a solution of glucose which has been compared with serum of known amylase activity. It is to be understood that glucose solution essentially evaluates only the color reagent.

| T-Tube (Test) | B-Tube (Blank) |
|---|---|
| 1. Add 0.050 ml. (50 microliters) serum. | 1. Add 0.050 ml. (50 microliters) serum. |
| 2. Add 0.50 ml. Substrate, pre-warmed at 37°C, mix well and place in water bath at 37°C. | 2. Add 0.50 ml DNSA reagent. Mix well. |
| 3. Exactly 15 minutes after adding substrate, add 0.50 ml. DNSA reagent. Mix well. | 3. Add 0.50 ml. substrate. Mix well. |
| 4. Heat 10 minutes at 100°C. | 4. Heat 10 minutes at 100°C. |
| 5. Cool in cold water bath for 3 minutes. | 5. Cool in cold water bath for 3 minutes. |
| 6. Add 4.00 ml. distilled water. Mix well. | 6. Add 4.00 ml. distilled water. Mix well. |
| 7. — | 7. Set absorbance at 0 in a colorimeter or spectrophotometer at 500 nm. |
| 8. Read absorbance at 500 nm against that of the corresponding blank. (Any absorbance between 470 and 560 nm can be used, but 500 nm is best.) (A 12-mm. round cuvet is used in a Coleman Jr. II spectrophotometer). | |
| 9. Calculation. If the graph of absorbance versus amylase activity is a straight line then the following equation can be used selecting; as the absorbance of the standard, any one of the representative values. $$\text{Amylase Activity of Sample, in Somogyi Units/100 ml.} = S X \frac{\text{(Absorbance of Sample versus its Blank)}}{\text{(Absorbance of Standard versus its Blank)}}$$ | |

S = given amylase activity of standard in Somogyi Units/100 ml.

If graph is not linear then the amylase activity is read from the graph. Serum amylase activity in excess of 120 Somogyi Units/100 ml. may indicate pancreatitis.

While there has above been described in detail a preferred embodiment of the present invention, it should be understood that the present invention is susceptible of various modifications. It is not intended to limit the invention to the specific embodiments theretofore disclosed. On the contrary, the invention is to cover all modifications and alternatives falling within the spirit and scope of the invention as expressed in the appended claims.

For example, while the invention has been illustrated with respect to DNSA color reagent, the use of which is desirable due to the virtual absence of protein interference, the advantages achieved thereby are believed to be equally applicable to other compounds reducible by the lower sugars which, in their reduced condition, exhibit a different color or intensity than in their unreduced form. The compounds, of course, should not be so easily reducible that they are reduced by EDTA or other ingredients present. Aromatic compounds containing a nitro group reducible to an amine or other colored substance are believed to be useful. Examples of such compounds include the following: 1,2-Dinitrobenzene; 3,4-Dinitrobenzoic Acid; 3,6-Dinitrophthalic Acid; 3,5-Dinitrosalicylic Acid (DNSA); 2,4,6-Trinitro-phenol (Picric Acid); 2,4-Dinitro-phenol; and 5,7-Dinitro-8-hydroxynaphthalene-2-sulfonate. Where protein exhibits a significant reducing effect on the compound, deproteinization should be accomplished prior to analysis.

It will also be appreciated that various other chelating compounds such as other derivatives of iminodiacetic acid can be substituted for all or part of the specifically illustrated EDTA. EDTA has the following structure

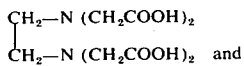

examples of other useful compounds include diethylene triamine pentacetic acid and ethylenebis (oxyethylene nitrilo) tetraacetic acid. EDTA is generally available as any of several salts or the free acid as well as hydrated and it can be used in any of these forms. Of course, the compounds selected should not contain groups having reducing properties such as aldehyde groups.

The amounts of color reagent and chelating compound employed in accomplishing the present invention are not particularly critical. For example, DNSA can be employed in about 0.1 – 0.3 grams/100 ml. of reagent solution, and, preferably, 0.15 – 0.20 gram. Similarly, on the same basis, EDTA is useful in an amount of about 0.1 – 0.4 grams and, preferably, 0.13 – 0.17 grams. It should be noted that these amounts of EDTA are considerably less than the quantity of Rochelle salt needed. The sulfite and salicylate are ordinarily used in about equal amounts of about 1–4 grams/100 ml., respectively. Other sulfite and salicylate salts, e.g., potassium, can be used in molarities substantially equivalent to the illustrated sodium salts. Regarding the quantity of sodium hydroxide and potassium hydroxide employed, it is necessary that a sufficient quantity of these bases be employed to elevate the pH of the solution to a value where the reducing effect of the lower sugars on the color reagent is enhanced. Typically, the pH should be above about 10 and preferably above 12. Accordingly, the combined amounts of sodium and potassium hydroxide should be greater than about 0.001 mole/100 ml.

However, while the total amount of hydroxide present is not particularly critical, it is an important aspect of the present invention that the molar ratio of the potassium hydroxide to sodium hydroxide be at least about 1 and preferably at least about 1.2 in order to avoid the appearance of particles as discussed above with substantially all types of human serum. While there is no upper limit on the ratio of potassium hydroxide to sodium hydroxide and there is no necessity for sodium hydroxide being present at all, from a cost point of view it is generally desirable to use the minimum amount of potassium hydroxide necessary to prevent particle formation and provide a color stable solution.

While the invention has been illustrated with the direct use of potassium hydroxide, it is believed that it is the presence of the potassium ion which prevents particle formation. Consequently, if potassium salts such as of the carbonate, sulfite, salicylate, etc. are used, the addition of potassium hydroxide can possibly be reduced or eliminated. In any event, it is believed that potassium ion concentration in the solution must be at least about 0.03 mole/100 ml. of solution and preferably at least about 0.04 mole. In addition to potassium other higher alkali metal cations (e.g., Rb, Cs, Fr) are thought to be useful but are economically unattractive.

I claim as my invention:

1. In a colorimetric process for the determination of amylase activity comprising adding a reagent solution containing an aromatic nitro compound reducible by lower sugars to an amylase hydrolyzed starch substrate and measuring the change in color or intensity; the improvement wherein the reagent solution comprises, in addition to the nitro compound, an iminodiacetic acid derivative chelating compound having substantially no reducing properties and at least about 0.03 mol./100 ml. of a higher alkali metal cation.

2. The process of claim 1 wherein the aromatic nitro containing compound is 1,2-dinitrobenzene; 3,4-dinitrobenzoic acid; 3,6-dinitrophthalic acid; 3,5-dinitrosalicylic acid; 2,4,6-trinitro-phenol; 2,4dinitrophenol; or 5,7-dinitro-8-hydroxynaphthalene-2-sulfonate.

3. The process of claim 2 wherein the aromatic nitro containing compound is 3,5-dinitrosalicylic acid.

4. The process of claim 1 wherein the acid derivative is ethylene diaminetetraacetic acid, diethylene triamine pentacetic acid or ethylenebis oxyethylene nitrilo tetraacetic acid.

5. The process of claim 3 wherein the acid derivative is ethylene diaminetetraacetic acid.

6. The process of claim 1 wherein the solution contains at least about 0.04 mol./100 ml. of potassium ion.

7. The process of claim 3 wherein the acid derivative is ethylene diaminetetraacetic acid.

8. The process of claim 7 wherein the solution contains potassium ions in a concentration of at least 0.04 mol./100 ml. of solution and wherein the molar ratio of potassium ion to any sodium ion present is at least about 1.

9. The process of claim 8 wherein the molar ratio of potassium ion to sodium ion, if present, is at least about 1.2.

10. The process of claim 9 wherein the solution contains, in addition to the ingredients included therein, salicylate ions, sulfite ions, carbonate ions and hydroxyl ions.

* * * * *